United States Patent [19]

Meisch

[11] Patent Number: 4,465,479
[45] Date of Patent: Aug. 14, 1984

[54] AIR VENT SPLASH GUARD FOR DRIP CHAMBER

[75] Inventor: Charles E. Meisch, Hasbrouck Heights, N.J.

[73] Assignee: C. R. Bard, Inc., Murray Hill, N.J.

[21] Appl. No.: 415,996

[22] Filed: Sep. 8, 1982

Related U.S. Application Data

[63] Continuation-in-part of Ser. No. 243,361, Mar. 13, 1981, abandoned.

[51] Int. Cl.³ .............................................. A61M 5/16
[52] U.S. Cl. .................................... 604/251; 604/325; 141/339
[58] Field of Search ................................ 604/251–255, 604/324–326, 86, 127, 415; 141/339, 285, 392

[56] References Cited

U.S. PATENT DOCUMENTS

| | | | |
|---|---|---|---|
| 2,208,989 | 7/1940 | Lewis | 141/285 |
| 2,214,708 | 9/1940 | Mayne et al. | 141/392 |
| 2,910,098 | 10/1959 | Wood | 141/285 |
| 3,042,038 | 7/1962 | Beacham | 604/127 |
| 3,142,296 | 7/1964 | Love | 128/214 |
| 3,834,386 | 9/1974 | Sisley | 604/86 |
| 3,880,317 | 4/1975 | Arnett | 141/392 |
| 4,198,971 | 4/1980 | Noiles | 604/251 |
| 4,305,403 | 12/1981 | Dunn | 604/324 |
| 4,395,260 | 7/1983 | Todd et al. | 604/252 |

*Primary Examiner*—C. Fred Rosenbaum
*Assistant Examiner*—Michelle N. Lester
*Attorney, Agent, or Firm*—Dennison, Meserole, Pollack & Scheiner

[57] ABSTRACT

A drip chamber splash guard comprising an annular member receivable within the upper end of the chamber. The guard has one periphery thereof engaged adjacent a centrally located drip sleeve depending below the vented top inwardly of the vents for maintenance of a free flow of air inwardly through the vents. The other periphery of the splash guard member engages adjacent the inner surface of the surrounding chamber outward of the vents. Limited air discharge openings are provided at spaced points about the guard whereby inwardly directed air flow is maintained through the splash guard itself while the filter vents are protected against gross or excessive splashing. In a preferred embodiment, the splash guard will be in the form of a truncated conical member with the air openings adjacent the chamber wall remote from the drip sleeve, the conical configuration, providing a tapered surface for a more effective deflecting of splash.

12 Claims, 5 Drawing Figures

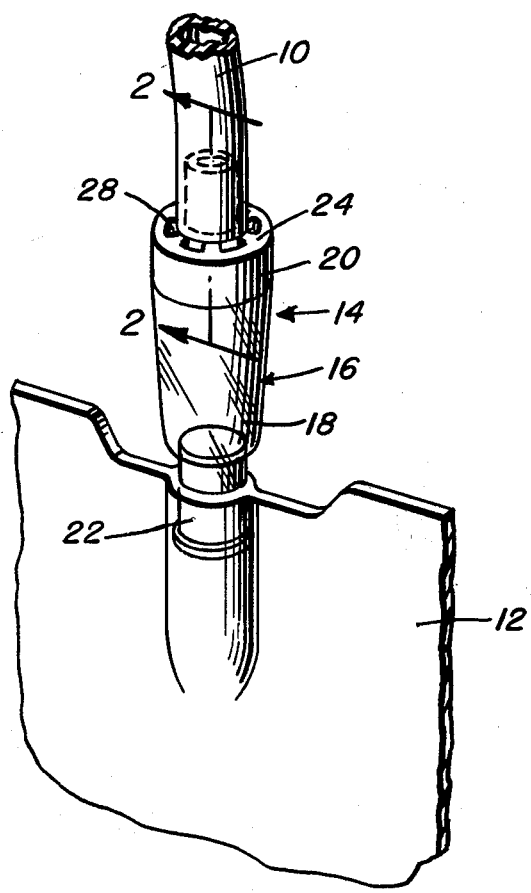
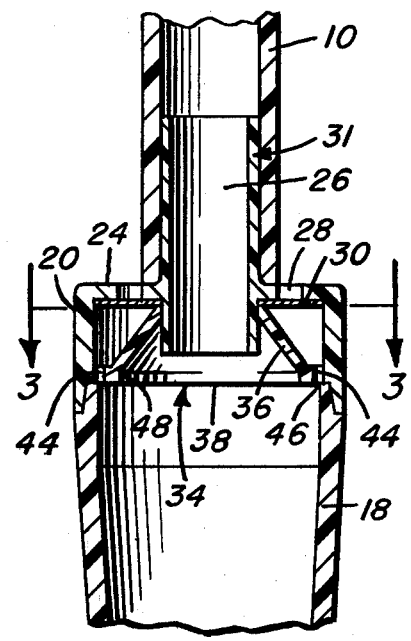
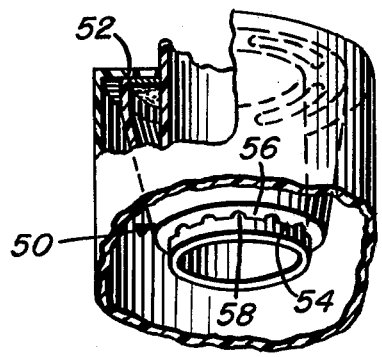
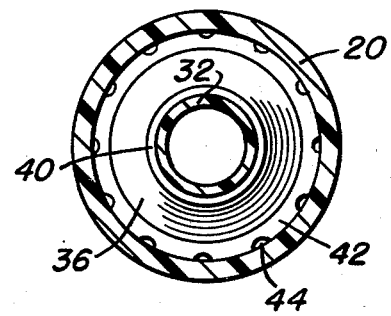
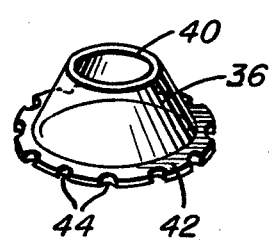

AIR VENT SPLASH GUARD FOR DRIP CHAMBER

This is a continuation-in-part of application Ser. No. 243,361, filed Mar. 13, 1981 now abandoned.

BACKGROUND OF THE INVENTION

The present invention generally relates to urine drainage systems, and is more specifically concerned with the drip chambers normally interposed between the drainage tube, extending from the patient, and the collection or urine bag. Such chambers function primarily to provide a break in the flow path of the liquid and thereby prevent backward movement of microbes, thus avoiding retrograde infection.

These drip chambers, as a means of enhancing movement of liquid therethrough and into the collection bag, incorporate, about the drainage tube receiving top thereof, filtered air vents. Such air vents, and more particularly the air permeable filter membranes associated therewith, tend to become clogged and/or contaminated. This problem of fouling of the air vent filters is especially prevalent when excessive or gross splashing is encountered. Such a situation in turn affects the air flow, and thus the operation of the system. More particularly, a contamination of the air vents and filters gives rise to the possibility of development of infection.

SUMMARY OF THE INVENTION

Prevention of contamination of the air vents and associated filters is the primary object of the present invention. Pursuant thereto, a splash guard is mounted within the drip chamber in surrounding depending relation relative to the filtered air vents. The splash guard, in the preferred form depends inwardly into the drip chamber from an upper inner edge sealed to the top, or the drip sleeve adjacent the top, to a lower, outer edge slightly below the lower end of the drip sleeve. At this lower edge, the splash guard is intimately engaged with the wall of the chamber peripherally thereabout and in a manner providing limited air ports at spaced points circumferentially about the chamber. These ports are positioned and configured to allow free downward flow of air, while at the same time restricting any upward movement of liquid from splashing, capillary attraction or the like, to the overlying vents.

The shielding function of the guard is enhanced by providing for a tapered configuration which forms a substantial downwardly directed under surface for deflection of the splashing liquid, in conjunction with a narrow air discharging lower end combined with a tapered upper surface which would greatly inhibit any upward movement of splashing liquid to the filtered air vents.

In a secondary embodiment, the splash guard is in the nature of an inverted truncated cone with the wide upper edge sealed to the top outward of the vents and with the lower edge sealed about the lower portion of the drip sleeve in a manner providing limited air ports.

Additional objects and advantages, for example the possible enhancement of inward air flow achieved by the tapered guard configuration, will become apparent from the following more detailed dscription of the construction and operation of the invention.

BRIEF DESCRIPTION OF DRAWINGS

FIG. 1 is a partial view of a drainage collection system illustrating a drip chamber incorporating the splash guard of the present invention;

FIG. 2 is a cross-sectional detail taken substantially on a plane passing along line 2—2 in FIG. 1;

FIG. 3 is a cross-sectional detail taken substantially on a plane passing along line 3—3 in FIG. 2;

FIG. 4 is a perspective view of the splash guard; and

FIG. 5 is a perspective view with portions broken away, of the upper portion of the drip chamber with a modified form of splash guard mounted thereto.

DESCRIPTION OF PREFERRED EMBODIMENT

FIG. 1 generally presents the environment of the invention illustrating, in a urine drainage or collection system, a drainage tube 10, a drainage or collection bag 12, and an interposed drip chamber 14. The remote end of the drainage tube 10 (not illustrated) is adapted for engagement with a patient.

The drip chamber 14 comprises a vertically elongated, normally transparent, body 16 having a main chamber 18 and a top portion 20 which may be integrally formed with the main chamber or formed as a separate opaque cap and bonded to the main chamber.

The lower end of the drip chamber is sealed within the drainage bag 12 in communication with the interior thereof, an appropriate tube extension 22 normally being associated with the bag received end of the drip chamber.

The top panel 24 of the drip chamber body 16 includes a central drainage receiving aperture 26 therethrough and a plurality of outwardly positioned and peripherally spaced air vents 28. Air permeable membranes 30 are associated with the vents 28 to both filter the incoming air and preclude an outward splashing of the liquid.

In order to assist in stabilizing and properly positioning the inner end of the drainage tube 10, an elongated rigid tube 31 extends through the top panel 24 and is sealed to the chamber top panel 24 to define the central aperture 26. This tube 31 extends centrally into the chamber in substantially spaced relation to the surrounding wall and defines a drip sleeve 32 well above the bottom of the chamber to provide for a free falling discharge of the liquid therefrom. The inner end portion of the drainage tube is received in sealed relation about the outer portion of the tube 31.

The construction as above described provides no protection against fouling of the filtered air vents, other than that inherent in the basic drip chamber construction and provided by a central positioning of the drip sleeve and the height of the chamber itself. Under conditions of gross or excessive splashing, there is a substantial possibility of fouling occurring in the drip chamber construction as thus far described. The present invention proposes avoidance of this problem by utilization of a splash guard 34.

In the preferred embodiment of splash guard 34, as illustrated in the drawings, the guard is basically of a hollow, truncated conical configuration presenting a downwardly and outwardly tapering body wall 36, an downwardly directed enlarged open base end 38, and a reduced upwardly opening upper end 40. The splash guard 34 is of a relatively thin walled construction with the tapered body wall 36 having an inner surface generally paralleling the outer surface to provide for a downwardly increasing under surface. The downwardly directed base end 40 includes an integral annular flange 42 defined peripherally thereabout and extending outwardly therefrom. This flange 42 is in turn provided with a series of arcuately configured outwardly directed air-passing ports 44 defined about and opening outwardly through the inner edge of the flange 44.

Noting FIGS. 2 and 3 in particular, the splash guard 34 is received within the upper portion or cap of the drip chamber 14 with the upper or truncated end 40 in intimate fluid-tight engagement with the under surface of the top panel 24, the drip sleeve immediately adjacent the top panel 24, or the junction therebetween, in inwardly spaced relation to the filtered air vents 28.

The lower enlarged base or end 40 of the splash guard 34 is positioned with the outer edge of the annular flange 42 in intimate engagement with the upper portion 20 of the chamber wall. This upper portion 20 may, as illustrated, be a separate cap bonded to the main chamber with the ported flange seated on a small lip or shoulder 46 at the juncture between the main chamber and cap. It will be appreciated that the overall height of the splash guard 34 is slightly greater than the length of projection of the drip sleeve 32 into the chamber. The air-passing ports 44 provide for a continued downward or inward discharge of the air into the drip chamber 14 itself.

With the annular flange in engagement with the chamber wall, it will be appreciatd that the guard 34 completely underlies the vents 28 through the top panel 24 with the air-passing ports 44 located laterally outward of the vents 28. As such, there is no straight line passage from the interior of the chamber through the vents.

At this point, attention is also directed to the inner periphery of the flange 44 which, at 48, defines a short depending vertical or cylindrical extension of the conical inner surface of the guard 34. This extension forms a vertical surface combining with the under surface of the flange 42 to define a sharp corner or edge. Configured in this manner, any drippage or splashing which might engage the under surface of the guard and not be immediately inwardly deflected therefrom, will directly drip inwardly into the chamber and not tend to travel to the air ports which provide for the desired inflow of air.

The positioning of the splash guard 34 to underlie the air vents 28, as described above, effectively encloses and protects the filtered air vents 28 against excess splashing of the liquid without encumbering, to any appreciable degree, the desired inflow of air. In fact, the funneling of the air flow, due to the basic conical configuration of the splash guard 34, may even enhance the air flow.

The actual retention of the splash guard 34 in position can be achieved by a bonding thereof at one or both of the peripheral edges to the inner surfaces engaged thereby. Alternatively, retention might rely on the support lip 46 and/or a tight frictional engagement with the exterior of the drip sleeve 32.

FIG. 5 illustrates a variation to the above described preferred embodiment wherein the splash guard, designated by reference numeral 50, is in the nature of an inverted truncated cone. The guard 50, also received within the upper portion of the drip chamber, is provided with the enlarged upper base end 52 in intimate fluid-tight engagement with the under surface of the top panel in surrounding outwardly spaced relation to the filtered air vents. The lower or truncated end 54 of the splash guard 50 is provided with an inwardly directed annular flange 56 in intimate engagement with a central drip sleeve peripherally thereabout and toward the lower end thereof. The annular flange 56 is provided, about the inner edge thereof, with a series of air-passing ports 58 which provide for the continued downward or inward movement of air into the drip chamber. As will be appreciated, the splash guard 50 provides for a splash deflecting tapered wall underlying, in spaced relation therebelow, the air vents, thus substantially contributing to the exclusion of any filter contaminating fluid.

While the illustrated embodiments of splash guards are considered particularly effective, in view of the splash-deflecting tapered under surface of the sloping wall and the opening restricting flange, sleeve encircling and vent enclosing splash guards of other specific configurations are also contemplated. For example, the wall of the splash guard may be other than of conical configuration. Also, other provisions might be made for the formation of the desired air-passing means at the lower end of the splash guard. Accordingly, it is not desired to limit the invention to the exact construction and operation shown and described. Rather, all suitable modifications and equivalents may be resorted to, falling within the scope of the invention as claimed.

I claim:

1. In a drip chamber, a top, a peripheral chamber wall depending from said top, drainage tube mounting means through said top for receiving and positioning an end of a drainage tube in communication with said chamber, air passing vent means through said top laterally of said drainage tube mounting means, and a splash guard positioned within said chamber below said top in splash-deflecting underlying relation to said vent means, said drainage tube mounting means including an aperture through said top with a drip sleeve depending from said top in surrounding relation to said aperture, said drip sleeve being located to one side of said vent means, said splash guard including an upper end positioned adjacent said top in spaced relation to said vent means, and located to the same side of said vent means as said drip sleeve, said splash guard terminating in a lower end portion vertically spaced below said top and positioned closely adjacent said chamber wall, and air passing means defined in the lower end portion of the splash guard, the aperture through the top, and the depending sleeve, being centrally located, said vent means surrounding said aperture and the upper end of said splash guard.

2. A drip chamber in accordance with claim 1 wherein the lower end portion of the splash guard surrounds said sleeve in outwardly spaced relation thereto.

3. A drip chamber in accordance with claim 2 wherein said lower end portion of the splash guard includes an outwardly directed flange terminating immediately adjacent said chamber wall, said air passing means being defined through said flange.

4. A drip chamber in accordance with claim 3 wherein said flange includes an outer peripheral edge, said air passing means being formed by peripherally spaced recesses defined in said edge.

5. A drip chamber in accordance with claim 4 wherein said splash guard tapers outwardly from approximately the upper end thereof to said lower end portion.

6. A drip chamber in accordance with claim 5 wherein said splash guard is of a generally conical configuration.

7. A drip chamber in accordance with claim 2 wherein said splash guard tapers outwardly from approximately the upper end thereof to said lower end portion.

8. In a drip chamber, a top, a peripheral chamber wall depending from said top, drainage tube mounting means through said top for receiving and positioning an end of a drainage tube in communication with said chamber, air passing vent means through said top laterally of said drainage tube mounting means, and a splash guard positioned within said chamber below said top in splash-deflecting underlying relation to said vent means, said drainage tube mounting means including an aperture through said top with a drip sleeve depending from said top in surrounding relation to said aperture, said drip sleeve being located to one side of said vent means, said splash guard including an upper end positioned adjacent said top in spaced relation to said vent means, and a lower end portion vertically spaced below said top, the aperture through the top, and the depending sleeve, being centrally located, said vent means surrounding said aperture and the upper end of said splash guard.

9. A drip chamber in accordance with claim 8 wherein the lower end portion of the splash guard surrounds said sleeve in outwardly spaced relation thereto.

10. A drip chamber in accordance with claim 9 wherein said lower end portion of the splash guard includes an outwardly directed flange terminating immediately adjacent said chamber wall, said air passing means being defined through said flange.

11. For use in a drip chamber having a top with a central depending drip sleeve opening therethrough and filtered vents peripherally thereabout, a splash guard, said splash guard including an elongated peripheral wall terminating in an upper end peripherally engageable with the top about the drip sleeve outward of the vents, and a lower end on said peripheral wall positionable in outwardly surrounding relation to the sleeve in spaced relation below the top, said lower end of said peripheral wall including an inwardly projecting peripheral flange, and air passing vent means defined through said flange.

12. The splash guard of claim 11 wherein said peripheral wall tapers inwardly from the upper end to the lower end thereof.

* * * * *